(12) United States Patent
Galan et al.

(10) Patent No.: US 6,664,386 B1
(45) Date of Patent: Dec. 16, 2003

(54) SYSTEM FOR EFFICIENT SECRETION OF RECOMBINANT PROTEINS

(75) Inventors: Jorge E. Galan, New Haven, CT (US); Wolf-Dietrich Hardt, Munich (DE)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/288,438

(22) Filed: Apr. 8, 1999

(51) Int. Cl.$^7$ ................. C07H 21/04; C12P 21/04; C12N 15/09
(52) U.S. Cl. ............ 536/23.4; 536/23.1; 536/23.7; 435/69.7; 435/71.1; 435/69.3; 435/69.8; 435/320.1
(58) Field of Search ................. 530/300, 350, 530/324, 825; 435/69.3, 69.1, 69.7, 69.8, 320.1; 536/23.4, 23.1, 23.7; 935/48, 47, 55, 66

(56) References Cited

U.S. PATENT DOCUMENTS

| | | | |
|---|---|---|---|
| 5,011,772 A | 4/1991 | Recsei | 435/69.1 |
| 5,143,830 A | 9/1992 | Holland et al. | 435/69.7 |
| 5,159,062 A | 10/1992 | Knapp et al. | 530/350 |
| 6,306,387 B1 * | 10/2001 | Galan | 424/93.2 |

OTHER PUBLICATIONS

Lazar et al. Mol. Cellular Biol. 8: 1247–1252, 1988.*
Valentine, P.J. et al., Vaccine 14(2):138–146 (1996).
Karem, K.L. et al., Journal of General Virology 78:427–434 (1997).
Ikonomidis, G., et al., J. Exp Med 180:2209–2218 (Dec. 1994).
Gentschev, I., et al., Behring Inst. Mitt 98:103–113 (1997).
Hess, J., et al., Proc Natl Acad Sci USA 93:1458–1463 (Feb. 1996).
Cornelis, G.R., Medicine/Sciences 11:1295–1304 (1995).
Cheng, L. W. et al., Molecular Microbiology 24(4):757–765 (1997).
Kubori, T., et al., Science 280:602–605 (Apr. 24, 1998).
Collazo, C.M., et al., Infection and Immunity 64(9):3524–3531 (Sep. 1996).
Collazo, C.M., et al., Molecular Microbiology 15(1):25–38 (1995).
Eichelberg, K., et al., Journal of Bacteriology 176(15):4501–4510 (Aug 1994).
Galan, J.E., Molecular Microbiolgy 20(2):263–271 (1996).
Galan, J.E. et al., Annu Rev Cell Dev Biol 12:221–255 (1996).
Galan, J.E. et al., Journal of Bacteriology 174(13):4338–4349 (Jul. 1992).
Ginocchio, C.C., et al., Cell 76:717–724 (Feb. 25, 1994).
Kaniga, K., et al., Journal of Bacteriology 177(24): 7078–7085 (Dec. 1995).
Kaniga, K., et al., Molecular Microbiology 13(4):555–568 (1994).
Kaniga, K., et al., Journal of Bacteriology 177(14):3965–3971 (Jul. 1995).
Kaniga, K., et al., Molecular Microbiology 21(3):633–641 (1996).
Wood, M.W., et al., Molecular Microbiology 22(2):327–338 (1996).
Selander, R.K., et al., In "*Escherichia coli* and Salmonella—Cellular and Molecular Biology", 2nd Ed., F. Neidhardt et al., Eds., ASM Press, Washington D.C., pp. 2691–2707 (1996).
Collazo, C.M., et al., Molecular Microbiology 24(4):747–756 (1997).
GenBank Accession No. AF043239 (Feb. 8,m 1998) and Accession No. AAC02071 (Feb. 6, 1998).
Russmann, H., et al., Science 281(5376):565–568 (Jul. 24, 1998).
Fu, Y., et al., Journal of Bacteriology 180(13):3393–3399 (Jul. 1998).
Hardt, W., et al., Proc Natl Acad Sci USA 95:2574–2579 (Mar. 1998).
Fu, Y., et al., Molecular Microbiology 27)20:359–368 (1998).
Hardt, W., et al., Proc Natl Acad Sci USA 94:9887–9892 (Sep. 1997).
Collazo, C.M., et al., Gene 192:51–59 (1997).

* cited by examiner

*Primary Examiner*—S. Devi
(74) *Attorney, Agent, or Firm*—Rogalsky & Weyand, LLP

(57) ABSTRACT

Provided is a signal peptide comprising an amino acid sequence at least 90% homologous to the amino acid sequence as shown in SEQ ID NO:1. Further provided is a fusion protein comprising the signal peptide fused to a heterologous protein. Also provided are nucleic acid molecules encoding the signal peptide and encoding the fusion protein, as well as vectors and recombinant host cells comprising the nucleic acid molecules. The recombinant host cell can be a recombinant bacterium having a functional type III secretion system and having loss-of-function mutations in genes that encode secreted substrate proteins of the type III secretion system. The recombinant host cell can be used in a method of producing the heterologous protein.

17 Claims, No Drawings

SYSTEM FOR EFFICIENT SECRETION OF RECOMBINANT PROTEINS

The subject invention was made with support under National Institute of Allergy and Infectious Disease Grant No. 5R01 AI30492 of the National Institutes of Health. The U.S. Government may have certain rights in this invention.

FIELD OF THE INVENTION

The subject invention is directed generally to a system for efficient secretion of recombinant proteins, and more particularly to a system which uses an engineered bacterium having a type III secretion system to export properly folded recombinant proteins into a culture supernatant.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Advances in recombinant DNA biotechnology have made it possible to produce a wide variety of useful polypeptide/protein products in host cells which have been transformed and transfected with DNA sequences which code for production of the polypeptide/protein products. Thus hormones (such as insulin, and growth hormones such as human growth hormone), and industrial or therapeutically useful enzymes (such as chymosin and tissue plasminogen activator (tPA)) have been produced using recombinant DNA technology.

Bacterial cells, in particular *Escherichia coli*, have been used as host cells for the production of recombinant polypeptide/protein products. The genetic systems of such bacterial cells are relatively well understood and such cells exhibit good growth characteristics. However, when such bacterial cells are used to overproduce foreign proteins, the foreign products typically accumulate within the host cells and it is usually necessary to disrupt the cells to effect recovery of the products. Also, recombinant products are often produced within bacterial host cells in the form of insoluble aggregates in which the polypeptides are not in their native, biologically functional form. It is necessary, therefore, to solubilize and denature/renature the insoluble polypeptide products to obtain useful products in soluble, native, biologically functional form. The processes of cell disruption and denaturation/renaturation add significantly to the cost of producing recombinant polypeptide products.

Attempts have been made, therefore, to develop bacterial expression systems which secrete recombinant products into the extracellular culture medium. For example, recombinant heterologous polypeptides have been expressed in bacteria as fusion proteins in which the heterologous polypeptide sequence is joined with an N-terminal signal sequence. However, such fusion proteins, although exported across the inner membrane in Gram-negative bacteria with concomitant removal of the signal sequence, fail to cross the outer membrane and therefore remain within the periplasm. Thus, it is still necessary to disrupt the host cells to effect recovery of heterologous recombinant products and denaturation/renaturation treatment may be required to yield products in native, biologically functional form.

'Leaky' mutants of Gram-negative bacterial host cells such as *Escherichia coli* have been proposed for use in the production and secretion of products to the extracellular medium. However, such mutant cells are often not suitable for large scale production of heterologous protein products since the yield of product is generally low and the fragility of the cells makes them unsuitable for growing on a large scale.

U.S. Pat. No. 5,143,830 attempts to address these problems by providing a process for the production of a polypeptide in which host cells are transformed with DNA coding for a fusion protein comprising the polypeptide and a further peptide comprising a C-terminal secretion sequence. The host cells are cultured to express and secrete the fusion protein therefrom. The C-terminal secretion sequence denotes a sequence of amino acids present in the C-terminus of a secreted polypeptide which sequence comprises essential information required for recognition and secretion of the secreted polypeptide via its secretion pathway. Preferably, the C-terminal secretion sequence is a haemolysin C-terminal secretion sequence (haemolysin is an extracellular protein toxin which is produced by some strains of *Escherichia coli*).

U.S. Pat. No. 5,159,062 also attempts to address these problems by providing a signal peptide from *Bordetella pertussis* which can be used for secretion of peptides in *Escherichia coli*.

Salmonella spp. have a specialized protein secretion system encoded at centisome 63 of the bacterial chromosome (reviewed in Galan 1996). This protein secretion system, termed type III, directs the export of a number of proteins. Characteristic features of this protein secretion system, which has also been identified in several other animal and plant pathogenic bacteria, include: 1) the absence in the secreted proteins of a typical, cleavable, sec-dependent, signal sequence; 2) the requirement of several accessory proteins for the export process; 3) the export of the target proteins through both the inner and outer membranes; and 4) the requirement of activating extracellular signals for its full function (reviewed in Galan 1996).

Currently known targets of bacterial type III secretion systems include the SptP, SipA, SipB, SipC, SipD, InvJ, SpaO, AvrA, and SopE proteins of Salmonella, the YopE, YopH, YopM and YpkA proteins of Yersinia spp. (Rosqvist et al. 1994; Sory and Cornelis 1994; Persson et al. 1995; Sory et al. 1995; Hakansson et al. 1996), the Ipa proteins of Shigella, and the ExoS proteins of *Pseudomonas aeruginosa*.

Given the continuing need and desire to efficiently produce large amounts of recombinant proteins, any system that can produce such large amounts of biologically functional proteins remains desirable.

SUMMARY OF THE INVENTION

The subject invention addresses this need by providing a signal peptide comprising an amino acid sequence at least 90% homologous to the amino acid sequence as shown in SEQ ID NO:1. In one embodiment, the amino acid sequence of the signal peptide is as shown in SEQ ID NO:1. Further provided is a fusion protein comprising the signal peptide fused to a heterologous protein. Also provided are nucleic acid molecules encoding the signal peptide, and encoding the fusion protein, as well as vectors and recombinant host cells comprising the nucleic acid molecules. The recombinant host cell can be a recombinant bacterium having a functional type III secretion system and having loss-of-function mutations in genes that encode secreted substrate proteins of the type III secretion system.

The recombinant host cell can be used in a method of producing a heterologous protein which method comprises culturing the recombinant host cell in a culture medium so as to obtain expression and secretion of the heterologous protein into the culture medium. The secreted heterologous protein can then be recovered from the culture medium.

Also provided is an isolated nucleic acid molecule of at least 45 nucleotides which specifically hybridizes with an isolated nucleic acid molecule having SEQ ID NO:2.

The recombinant bacterium useful for producing heterologous proteins in accordance with the subject invention is also provided. The recombinant bacterium preferably has a functional type III secretion system and has loss-of-function mutations in genes that encode secreted substrate proteins of the type III secretion system.

DETAILED DESCRIPTION OF THE INVENTION

The term "nucleic acid", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA, and nonfunctional DNA or RNA.

"Isolated" nucleic acid refers to nucleic acid which has been separated from an organism in a substantially purified form (i.e. substantially free of other substances originating from that organism), and to synthetic nucleic acid.

By a nucleic acid sequence "homologous to" or "complementary to", it is meant a nucleic acid that selectively hybridizes, duplexes or binds to DNA sequences encoding the signal peptide or portions thereof when the DNA sequences encoding the signal peptide are present in a human genomic or cDNA library. A DNA sequence which is similar or complementary to a target sequence can include sequences which are shorter or longer than the target sequence so long as they meet the functional test set forth.

Typically, the hybridization is done in a Southern blot protocol using a 0.2×SSC, 0.1% SDS, 65° C. wash. The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9 M sodium chloride and 120 mM sodium citrate. 0.2×SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein or peptide. The nucleic acid molecule includes both the full length nucleic acid sequences as well as non-full length sequences derived from the full length peptide. It being further understood that the sequence includes the degenerate codons of the native sequence or sequences which may be introduced to provide codon preference in a specific host cell.

The term "located upstream" as used herein refers to linkage of a promoter upstream from a nucleic acid (DNA) sequence such that the promoter mediates transcription of the nucleic acid (DNA) sequence.

The term "vector", refers to viral expression systems, autonomous self-replicating circular DNA (plasmids), and includes both expression and nonexpression plasmids. Where a recombinant microorganism or cell is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or the vector may be incorporated within the host's genome.

The term "plasmid" refers to an autonomous circular DNA molecule capable of replication in a cell, and includes both the expression and nonexpression types. Where a recombinant microorganism or cell is described as hosting an "expression plasmid", this includes latent viral DNA integrated into the host chromosome(s). Where a plasmid is being maintained by a host cell, the plasmid is either being stably replicated by the cell during mitosis as an autonomous structure, or the plasmid is incorporated within the host's genome.

The phrase "heterologous protein" or "recombinantly produced heterologous protein" refers to a peptide or protein of interest produced using cells that do not have an endogenous copy of DNA able to express the peptide or protein of interest. The cells produce the peptide or protein because they have been genetically altered by the introduction of the appropriate nucleic acid sequences. The recombinant peptide or protein will not be found in association with peptides or proteins and other subcellular components normally associated with the cells producing the peptide or protein.

The following terms are used to describe the sequence relationships between two or more nucleic acid molecules or polynucleotides, or between two or more amino acid sequences of peptides or proteins: "reference sequence", "comparison window", "sequence identity", "sequence homology", "percentage of sequence identity", "percentage of sequence homology", "substantial identity", and "substantial homology". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted, for example, by the local homology algorithm of Smith and Waterman (1981), by the homology alignment algorithm of Needleman and Wunsch (1970), by the search for similarity method of Pearson and Lipman (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to nucleic acid molecules or polynucleotides, the terms "substantial identity" or "substantial sequence identity" mean that two nucleic acid sequences, when optimally aligned (see above), share at least 90 percent sequence identity, preferably at least 95 percent sequence identity, more preferably at least 96, 97, 98 or 99 percent sequence identity.

"Percentage nucleotide (or nucleic acid) identity" or "percentage nucleotide (or nucleic acid) sequence identity" refers to a comparison of the nucleotides of two nucleic acid molecules which, when optimally aligned, have approximately the designated percentage of the same nucleotides. For example, "95% nucleotide identity" refers to a comparison of the nucleotides of two nucleic acid molecules which when optimally aligned have 95% nucleotide identity.

Preferably, nucleotide positions which are not identical differ by redundant nucleotide substitutions (the nucleotide substitution does not change the amino acid encoded by the particular codon).

As further applied to nucleic acid molecules or polynucleotides, the terms "substantial homology" or "substantial sequence homology" mean that two nucleic acid sequences, when optimally aligned (see above), share at least 90 percent sequence homology, preferably at least 95 percent sequence homology, more preferably at least 96, 97, 98 or 99 percent sequence homology.

"Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides which are not identical but differ by redundant nucleotide substitutions (the nucleotide substitution does not change the amino acid encoded by the particular codon). For example, "95% nucleotide homology" refers to a comparison of the nucleotides of two nucleic acid molecules which when optimally aligned have 95% nucleotide homology.

As applied to polypeptides, the terms "substantial identity" or "substantial sequence identity" mean that two peptide sequences, when optimally aligned, such as by the programs GAP or BESTFIT using default gap, share at least 90 percent sequence identity, preferably at least 95 percent sequence identity, more preferably at least 96, 97, 98 or 99 percent sequence identity.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

As further applied to polypeptides, the terms "substantial homology" or "substantial sequence homology" mean that two peptide sequences, when optimally aligned, such as by the programs GAP or BESTFIT using default gap, share at least 90 percent sequence homology, preferably at least 95 percent sequence homology, more preferably at least 96, 97, 98 or 99 percent sequence homology.

"Percentage amino acid homology" or "percentage amino acid sequence homology" refers to a comparison of the amino acids of two polypeptides which, when optimally aligned, have approximately the designated percentage of the same amino acids or conservatively substituted amino acids. For example, "95% amino acid homology" refers to a comparison of the amino acids of two polypeptides which when optimally aligned have 95% amino acid homology. As used herein, homology refers to identical amino acids or residue positions which are not identical but differ only by conservative amino acid substitutions. For example, the substitution of amino acids having similar chemical properties such as charge or polarity are not likely to affect the properties of a protein. Examples include glutamine for asparagine or glutamic acid for aspartic acid.

The phrase "substantially purified" or "isolated" when referring to a protein (or peptide), means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein (or peptide) which is the predominant species present in a preparation is substantially purified. Generally, a substantially purified or isolated protein (or peptide) will comprise more than 80% of all macromolecular species present in the preparation. Preferably, the protein (or peptide) is purified to represent greater than 90% of all macromolecular species present. More preferably the protein (or peptide) is purified to greater than 95%, and most preferably the protein (or peptide) is purified to essential homogeneity, wherein other macromolecular species are not detected by conventional techniques.

"Biological sample" as used herein refers to any sample obtained from a living organism or from an organism that has died. Examples of biological samples include body fluids and tissue specimens.

As used herein, an "avirulent" bacterium refers to a bacterium which is not capable of causing disease in the host to which it is administered.

As further used herein, a "Salmonella encoding" refers to a Salmonella which has nucleic acid therein which encodes the referenced protein or peptide, either as extrachromosomal nucleic acid or as nucleic acid incorporated into the genome of the Salmonella.

This invention provides a nucleic acid molecule of at least 45 nucleotides capable of specifically hybridizing with an isolated DNA molecule having SEQ ID NO:2 (which encodes the signal peptide). In one embodiment, the molecule is DNA. In another embodiment, the molecule is RNA. In another embodiment the nucleic acid molecule may be 45–60 nucleotides in length. In another embodiment the nucleic acid molecule may be 60–90 or more nucleotides in length. This invention also provides the nucleic acid molecule of at least 45 nucleotides capable of specifically hybridizing with a nucleic acid molecule which is complementary to the isolated DNA molecule which encodes the signal peptide.

The nucleic acid molecule of at least 45 nucleotides may specifically hybridize with moderate to high stringency to at least a portion of the nucleic acid molecule with a sequence shown in SEQ ID NO:2 (the nucleic acid sequence of the signal peptide of one embodiment of the subject invention).

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. High stringency may be attained, for example, by overnight hybridization at about 68° C. in a 6×SSC solution, washing at room temperature with 6×SSC solution, followed by washing at about 68° C. in a 6×SSC solution then in a 0.6×SSX solution.

Hybridization with moderate stringency may be attained, for example, by: 1) filter pre-hybridizing and hybridizing with a solution of 3× sodium chloride, sodium citrate (SSC), 50% formamide, 0.1M Tris buffer at pH 7.5, 5×Denhardt's solution; 2) pre-hybridization at 37° C. for 4 hours; 3) hybridization at 37° C. with amount of labelled probe equal to 3,000,000 cpm total for 16 hours; 4) wash in 2×SSC and 0.1% SDS solution; 5) wash 4× for 1 minute each at room temperature and 4× at 60° C. for 30 minutes each; and 6) dry and expose to film.

The phrase "selectively hybridizing to" refers to a nucleic acid molecule that hybridizes, duplexes or binds only to a particular target DNA or RNA sequence when the target sequences are present in a preparation of total cellular DNA or RNA. By selectively hybridizing it is meant that a nucleic acid molecule binds to a given target in a manner that is detectable in a different manner from non-target sequence under moderate, or more preferably under high, stringency conditions of hybridization. "Complementary" or "target" nucleic acid sequences refer to those nucleic acid sequences which selectively hybridize to a nucleic acid molecule. Proper annealing conditions depend, for example, upon a nucleic acid molecule's length, base composition, and the number of mismatches and their position on the molecule, and must often be determined empirically. For discussions of nucleic acid molecule (probe) design and annealing conditions, see, for example, Sambrook et al. 1989 or Ausubel et al. 1987.

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the signal peptide or other peptide/protein to which the relevant sequence listing relates.

The DNA molecules of the subject invention also include DNA molecules coding for polypeptide analogs, fragments or derivatives of polypeptides which differ from naturally-occurring forms (the naturally-occurring signal peptide) in terms of the identity or location of one or more amino acid residues (deletion analogs containing less than all of the residues specified for the protein, substitution analogs wherein one or more residues specified are replaced by other residues, and addition analogs wherein one or more amino acid residues is added to a terminal or medial portion of the polypeptides) and which share the signal property of the naturally-occurring form. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

With these understandings in mind, the subject invention provides a signal peptide comprising an amino acid sequence at least 90% homologous to the amino acid sequence as shown in SEQ ID NO:1. In one embodiment, the signal peptide comprises an amino acid sequence as shown in SEQ ID NO:1. This signal sequence is derived from the SopE protein of *Salmonella typhimurium*. The SopE protein is a protein which is secreted via the type III secretion system of *Salmonella typhimurium*. The signal sequence has the unusual property of directing the secretion of virtually unlimited amounts of a produced protein, especially when the protein is expressed in the recombinant *Salmonella typhimurium* strain described below.

The signal sequence as claimed herein has a sequence which comprises essential information required for recognition and secretion of the secreted heterologous protein via the type III secretion pathway.

In its broader sense, therefore, the invention provides a signal peptide comprising an amino acid sequence with substantial homology to the amino acid sequence as shown in SEQ ID NO:1. A signal peptide comprising an amino acid sequence as shown in SEQ ID NO:1 or comprising an amino acid sequence at least 90% homologous to the amino acid sequence as shown in SEQ ID NO:1 is specifically intended to exclude the full length naturally-occurring SopE protein of *Salmonella typhimurium* with its signal peptide. A signal peptide as claimed herein is intended to cover much shorter amino acid sequences, and generally will be less than 100 amino acids in length, and more preferably less than 75 amino acids in length.

Although the signal peptide described and claimed herein was derived from Salmonella typhimurium, having now identified the amino acid sequence of the signal peptide, the signal peptide can be constructed using conventional genetic engineering techniques. For example, a nucleic acid sequence encoding the desired amino acid sequence can be synthesized using an oligonucleotide synthesizer and engineered into a vector (such as a plasmid vector) for incorporation into a bacteria having a type III secretion system. Alternatively, the nucleic acid sequence encoding the signal peptide could be isolated from the DNA (sopE gene) of a *Salmonella typhimurium* organism by appropriate restriction enzyme digestion or PCR of genomic DNA.

The purpose/use of the signal peptide claimed herein is to effect the secretion of a heterologous protein. A heterologous protein, as used herein, refers to a protein of interest or any desirable portion of a protein of interest, and is intended to cover peptides (short "proteins") and proteins of any desirable length. The protein of interest is selected based on the desirability of expressing large amounts of a particular protein (including, for example, hormones, enzymes, and interleukins; including, for example, insulin, human growth hormone, tissue plasminogen activator, etc.).

The invention thus further provides a fusion protein comprising the signal peptide fused to a heterologous protein, wherein the signal peptide comprises an amino acid sequence with substantial homology to the amino acid sequence as shown in SEQ ID NO:1. Preferably, the signal peptide comprises an amino acid sequence as shown in SEQ ID NO:1. As used herein, a fusion protein refers in its art-recognized sense to a signal peptide "fused" to a heterologous protein, where "fused" refers to a continuous amino acid sequence which includes the amino acid sequence of the signal peptide and the amino acid sequence of the heterologous protein. The fusion protein may comprise an internal fusion protein (in which the signal peptide is within the heterologous protein), an N-terminal fusion protein (in which the signal peptide is joined to the N-terminus of the heterologous protein), or a C-terminal fusion protein (in which the signal peptide is joined to the C-terminus of the heterologous protein). An N-terminal fusion protein is presently preferred. Typically and as used herein, fusion proteins comprise selective cleavage sites at the junction or junctions between the amino acid sequence of the signal peptide and the amino acid sequence of the heterologous protein. Such selective cleavage sites may comprise one or more amino acid residues which provide a site susceptible to selective enzymatic, chemical or other cleavage. The fusion protein may be further processed to cleave the heterologous protein therefrom; for example, if the heterologous protein is required without additional amino acid residues.

As indicated above, additional amino acids which do not adversely affect the secretory function of the signal peptide could be included within the amino acid sequence of the fusion protein, and additional amino acids which do not adversely affect the function of the heterologous protein could be included within the amino acid sequence of the fusion protein. The inclusion of additional amino acids in the fusion protein, other than the particular amino acids of the signal peptide and of the heterologous protein, which additional amino acids do not adversely affect the intended function of the signal peptide and of the secreted heterologous protein, is not intended to circumvent the language "fusion protein" as used and as claimed herein. For example, additional amino acids may be included in the fusion protein which separate the signal peptide from the heterologous protein in order to provide a favored steric configuration in the fusion protein which promotes the secretion process. The number of such additional amino acids which serve as separators may vary, and generally would not exceed 60 amino acids.

The invention further provides an isolated nucleic acid molecule encoding the signal peptide (the signal peptide having an amino acid sequence with substantial homology to the amino acid sequence as shown in SEQ ID NO:1). Preferably, the isolated nucleic acid molecule encodes a signal peptide having an amino acid sequence as shown in SEQ ID NO:1. In one embodiment, the isolated nucleic acid molecule has a nucleotide sequence as shown in SEQ ID NO:2. Further provided is an isolated nucleic acid molecule encoding the fusion protein (the fusion protein comprising the signal peptide fused to a heterologous protein).

The methods by which DNA sequences may be obtained and linked to provide the DNA sequence encoding the fusion protein are well known in the field of recombinant DNA technology. As indicated above, DNA encoding the signal peptide may be synthesized using an oligonucleotide synthesizer, may be isolated from the DNA (sopE gene) of a *Salmonella typhimurium* organism by appropriate restriction enzyme digestion, or may be obtained from *Salmonella typhimurium* cells by PCR of genomic DNA with the appropriate primers. Likewise, the DNA encoding the heterologous protein may be synthesized using an oligonucleotide synthesizer (if the length of the DNA is short enough to make this feasible), may be isolated from the DNA of a parent cell which produces the protein by appropriate restriction enzyme digestion, or may be obtained from the parent cells by PCR of genomic DNA with the appropriate primers. Additional DNA sequences which code for one or more selective cleavage sites at the junction or junctions between the DNA sequence of the signal peptide and the DNA sequence of the heterologous protein may also be incorporated into the DNA encoding the fusion protein (see above discussion).

Having thus described the nucleic acid molecule according to the subject invention, the nucleic acid molecule can be provided in the form of a vector (which comprises the nucleic acid molecule). One example of such a vector is a plasmid. A recombinant host cell which comprises the vector is also provided. Preferably, the recombinant host cell is a bacterium having a functional type III secretion system. The bacterium preferably also has loss-of-function mutations in genes that encode secreted substrate proteins of the type III secretion system. Preferably, the bacterium is *Salmonella typhimurium.* The recombinant host cell can further comprise nucleic acid encoding a regulatable (inducible) promoter located upstream of the nucleic acid molecule encoding the fusion protein, to permit expression and secretion of the heterologous protein to be controlled by inducing the promoter (which directs the expression of the heterologous protein).

Standard laboratory techniques known in the art of recombinant DNA and bacterial genetics can be used to construct the fusion proteins and recombinant bacteria and to introduce a nucleic acid molecule encoding a fusion protein into a recombinant bacterium (see Sambrook et al. 1989). One commonly used method for introducing nucleic acid molecules into a cell is through the use of a plasmid vector. The use of viral vectors such as bacteriophage is another example of a known method for introducing nucleic acid molecules into a cell (the bacteriophage is used to introduce nucleic acid molecules into a bacterial cell).

The invention further provides a method of producing a heterologous protein. The method comprises culturing the recombinant bacterium described above (which includes the DNA encoding the fusion protein) in a culture medium so as to obtain expression and secretion of the heterologous protein into the culture medium. The heterologous protein can be readily isolated (see above) (recovered in a form substantially free from other proteins) from the culture medium since it constitutes the vast majority of the protein accumulated in this fraction (because the secretion machinery of the recombinant bacterium exclusively directs the secretion of the fusion protein which includes the heterologous protein). This secreted heterologous protein is properly folded and biologically active and therefore denaturation/renaturation steps are not necessary.

The signal peptide described herein is derived from the SopE protein of *Salmonella typhimurium,* and in its native state directs the secretion of the SopE protein via the type III secretion system of *Salmonella typhimurium.* This signal peptide, however, can be used to effect the secretion of a heterologous protein from any bacterium having a functional type III secretion system (see Galan 1996; Rosqvist et al. 1994; Sory and Cornelis 1994; Persson et al. 1995; Sory et al. 1995; Hakansson et al. 1996; and Galan and Bliska 1996 for discussions of type III secretion systems suitable for use in the subject invention). Any type III secretion systems known to exist and yet to be discovered are examples of "type III secretion systems" in accordance with the subject invention. For example, currently known targets of bacterial type III secretion systems include the SptP, SipA, SipB, SipC, SipD, InvJ, SpaO, AvrA, and SopE proteins of Salmonella, the Yop and Ypk proteins of Yersinia (for example, YopE, YopH, YopM and YpkA), the Ipa proteins of Shigella, and the ExoS proteins of *Pseudomonas aeruginosa.*

The invention thus further provides a recombinant bacterium having a functional type III secretion system and having loss-of-function mutations in genes that encode secreted substrate proteins of the type III secretion system. Such an engineered recombinant bacterium is particularly useful for production and secretion of large amounts of a heterologous protein using the signal peptide disclosed herein. The recombinant bacterium has a functional type III secretion system, through which it naturally would secrete substrate proteins of its type III secretion system. The genetic make-up of the bacterium is mutated so that the genes encoding these substrate proteins do not express the substrate proteins. Therefore, when heterologous proteins fused to the signal peptide of the subject invention are expressed in the recombinant bacterium, the type III secretion machinery exclusively directs the secretion of the heterologous proteins containing the above-described signal peptide. In a presently preferred embodiment, the recombinant bacterium is *Salmonella typhimurium* and the loss-of-function mutations are in the genes that encode secreted substrate proteins of the type III secretion system of *Salmonella typhimurium* (including the sipA, sipB, sipC, sipD, sptP, avrA and sopE genes). In wild-type *Salmonella typhimurium,* the type III secretion system requires the presence of an activating signal for full activity (Zierler and Galan 1995). However, the presence of the sipD mutation in the recombinant *Salmonella typhimurium* strain renders the system active in the absence of the activating signal thereby facilitating abundant secretion of the heterologous protein. Further examples of recombinant bacteria according to the subject invention include Yersinia spp. in which the loss-of-function mutations are in the genes that encode secreted substrate proteins of the type III secretion system of Yersinia spp. (including the yopE, yopH, yopM and ypkA genes); Shigella spp. in which the loss-of-function mutations are in the genes that encode secreted substrate proteins of the type III secretion system of Shigella spp. (including the ipa gene); and *Pseudomonas aeruginosa* in which the loss-of-function mutations are in the genes that encode secreted substrate proteins of the type III secretion system of *Pseudomonas aeruginosa* (including the exoS gene). Loss-of-function mutations in the genes that encode secreted substrate proteins of the type III secretion system can be effected using standard laboratory techniques.

As indicated above, these recombinant bacterium are particularly useful for the production of large amounts of heterologous protein. The signal peptide disclosed herein directs the secretion of the heterologous protein from the recombinant bacterium via their type III secretion system. The invention thus further provides the recombinant bacterium described above further comprising DNA encoding a fusion protein, wherein the fusion protein comprises the signal peptide fused to the heterologous protein. Using standard recombinant DNA techniques, the DNA encoding the heterologous protein can be cloned downstream of the segment of DNA encoding the signal peptide. The expression of the heterologous protein can be directed by a fully regulatable strong promoter. In this embodiment, the recombinant bacterium further comprises DNA encoding a regulatable promoter located upstream of the DNA encoding the fusion protein (the signal peptide and the heterologous protein). The presently preferred promoter is derived from the araABC operon of *Escherichia coli*, although other suitable promoters known in the art can also be used. Upon induction of the regulatable promoter, the heterologous protein is secreted from the recombinant bacterium.

Avirulent strains of *Salmonella typhimurium* are being considered as vectors for the delivery of heterologous proteins (antigens) to thereby serve as multivalent recombinant vaccines. It has been observed that the bacterial compartment where the heterologous protein is expressed has significant influence on the quality of the immune response obtained (reviewed in Doggett and Curtiss 1992). Thus, in several instances secretion of the heterologous proteins (antigens) has been shown to increase the immunogenicity of the recombinant avirulent Salmonella vaccine strains. The system described herein can be adapted to be used in the context of avirulent Salmonella vaccine strains to direct the secretion of heterologous protein (antigen). Unlike other secretion systems used to export antigens in Salmonella vaccine strains which are based on heterologous secretion systems, the system described herein is based on a protein secretion machinery naturally occurring in all Salmonella strains. This has many advantages as it does not require the cloning of additional foreign genes encoding heterologous secretory functions into the Salmonella vaccine stains to obtain secretion of the heterologous protein. The recombinant Salmonella spp. can be introduced into a host (in which an immune response is desired to the heterologous protein) by any methods known in the art, including for example, oral infection or injection.

The technology of the subject invention has several advantages over other existing technologies. These advantages include: a) the system directs the secretion of folded proteins which accumulate in the culture supernatant; b) the system is more efficient than other systems as virtually all protein produced is secreted; c) the system can be easily used in massive fermentor-type settings for industrial production of proteins; d) since laboratory strains of *Salmonella typhimurium* are competent for secretion, these strains can be safely used in a biotechnology setting without the need for extra biohazard precautions; and e) the system can be used in conjunction with recombinant avirulent Salmonella vaccine strains for the secretion of recombinant antigens.

EXAMPLE

The plasmid pSB1198 which encodes the first 70 amino acids of SopE fused to alkaline phosphatase (PhoA) lacking its amino-terminal signal sequence, was introduced into wild type *S. typhimurium* and its mutant derivatives SB245 and SB161. The mutant strain-SB245 carries null-mutations in the genes encoding the major *S. typhimurium* type III secreted proteins and the mutant strain SB161 carries a mutation in invG, an essential component of the type III secretion apparatus (Kaniga et al. 1994). Whole cell lysates and culture supernatants of these strains were examined for the presence of PhoA by western immunoblot analysis. It was found that the majority of the SopE-PhoA fusion was recovered from the culture supernatants of SB245 and wild type *S. typhimurium* strains although it was not recovered from supernatants of the invG mutant strain. These results indicate that the signal sequence present within the first 70 amino acids of SopE is capable of directing the secretion of a heterologous protein.

In a related set of experiments, an epitope (M45) derived from the Adeno virus E4-6/7 protein (Obert et al. 1994) was fused to the first 59 amino acids of SopE. The resulting plasmid, pSB1185, was introduced into wild-type *S. typhimurium* and its mutant derivatives SB245 and SB161. Whole cell lysates and culture supernatants of these strains were examined for the presence of the fusion protein by western immunoblot analysis using an antibody directed to the viral epitope. It was found that the majority of the SopE-M45 fusion protein was recovered from the culture supernatants of SB245 and wild-type *S. typhimurium* strains although it was not recovered from supernatants of the invG mutant strain. These results further demonstrate the ability of the SopE signal sequence to direct the secretion of heterologous proteins.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

Ausubel, F., et al., Current Protocols in Molecular Biology, New York (1987).
Doggett, T. A. and Curtiss, R., *Adv Exp Med Biol* 327:165–173 (1992).
Galan, J. E., *Molecular Microbiol* 20:263–271 (1996).
Galan, J. E. and Bliska, J. B., *Ann Rev Cell Dev Biol* 12:219–253 (1996).
Hakansson, S., et al., *Mol Microbiol* 20:593–603 (1996).
Kaniga, K., et al., *Mol Microbiol* 13:555–568 (1994).
Needleman and Wunsch, J Mol Biol 48:443 (1970).
Obert, S., et al., *Molec Cell Biol* 14:1333–1346 (1994).
Pearson and Lipman, Proc Natl Acad Sci USA 85:2444 (1988).
Persson, C., et al., *Molecular Microbiol* 18:135–150 (1995).
Rosqvist, R., et al., *EMBO J* 13:964–972 (1994).
Sambrook, et al., *Molecular Cloning: A Laboratory Manual*, 2d Edition, Cold Spring Harbor Laboratory Press, Cold Spring Harbor, N.Y. (1989).

Smith and Waterman, Adv Appl Math 2:482 (1981).

Sory, M.-P., et al., *Proc Natl Acad Sci USA* 92:11998–12002 (1995).

Sory, M.-P. and Cornelis, G. R., *Molec Microbiol* 14:583–594 (1994).

Zierler, M. and Galan, J. E., *Infect Immun* 63:4024–4028 (1995).

What is claimed is:

1. An isolated nucleic acid molecule encoding a signal peptide having an amino acid sequence consisting of SEQ ID NO:1.

2. An isolated nucleic acid molecule encoding a fusion protein, the fusion protein comprising a signal peptide fused to a heterologous protein, wherein the signal peptide has an amino acid sequence consisting of SEQ ID NO:1.

3. A vector comprising the isolated nucleic acid molecule of claim 2.

4. A recombinant host cell comprising the vector of claim 3.

5. The recombinant host cell of claim 4 wherein the host cell is a bacterium having a functional type III secretion system and having loss-of-function mutations in genes that encode secreted substrate proteins of the type III secretion system.

6. The recombinant host cell of claim 5 wherein the bacterium is *Salmonella typhimurium*.

7. The recombinant host cell of claim 4 further comprising a nucleic acid molecule encoding a regulatable promoter located upstream of the nucleic acid molecule encoding the fusion protein.

8. The recombinant host cell of claim 6 wherein the genes include the sipA, sipB, sipC, sipD, sptP, avrA and sopE genes.

9. The isolated nucleic acid molecule of claim 1 wherein the nucleic acid molecule has a nucleotide sequence as shown in SEQ ID NO:2.

10. An isolated nucleic acid molecule encoding a signal peptide having an amino acid sequence less than 100 amino acids in length and comprising SEQ ID NO:1.

11. An isolated nucleic acid molecule encoding a fusion protein, the fusion protein comprising a signal peptide fused to a heterologous protein, wherein the signal peptide has an amino acid sequence less than 100 amino acids in length and comprises SEQ ID NO:1.

12. A vector comprising the isolated nucleic acid molecule of claim 11.

13. A recombinant host cell comprising the vector of claim 12.

14. The recombinant host cell of claim 13 wherein the host cell is a bacterium having a functional type III secretion system and having loss-of-function mutations in genes that encode secreted substrate proteins of the type III secretion system.

15. The recombinant host cell of claim 14 wherein the bacterium is *Salmonella typhimurium*.

16. The recombinant host cell of claim 15 wherein the genes include the sipA, sipB, sipC, sipD, sptP, avrA and sopE genes.

17. The recombinant host cell of claim 14 further comprising a nucleic acid molecule encoding a regulatable promoter located upstream of the nucleic acid molecule encoding the fusion protein.

* * * * *

SEQUENCE LISTING

```
<160> NUMBER OF SEQ ID NOS: 2

<210> SEQ ID NO 1
<211> LENGTH: 59
<212> TYPE: PRT
<213> ORGANISM: Salmonella typhimurium

<400> SEQUENCE: 1

Val Thr Lys Ile Thr Leu Ser Pro Gln Asn Phe Arg Ile Gln Lys Gln
 1               5                  10                  15

Glu Thr Thr Leu Leu Lys Glu Lys Ser Thr Glu Lys Asn Ser Leu Ala
                20                  25                  30

Lys Ser Ile Leu Ala Val Lys Asn His Phe Ile Glu Leu Arg Ser Lys
            35                  40                  45

Leu Ser Glu Arg Phe Ile Ser His Lys Asn Thr
        50                  55

<210> SEQ ID NO 2
<211> LENGTH: 177
<212> TYPE: DNA
<213> ORGANISM: Salmonella typhimurium

<400> SEQUENCE: 2
gtgacaaaaa taactttatc tccccagaat tttagaatcc aaaaacagga aaccacacta         60
ctaaaagaaa aatcaaccga gaaaaattct ttagcaaaaa gtattctcgc agtaaaaaat        120
cacttcatcg aattaaggtc aaaattatcg gaacgtttta tttcgcataa gaacact           177
```